(12) United States Patent
Chern-Lin et al.

(10) Patent No.: US 10,207,023 B2
(45) Date of Patent: Feb. 19, 2019

(54) ANTIBACTERIAL CALCIUM-BASED MATERIALS

(71) Applicant: NATIONAL CHENG KUNG UNIVERSITY, Tainan (TW)

(72) Inventors: Jiin-Huey Chern-Lin, Winnetka, IL (US); Chien-Ping Ju, Kansas City, MO (US); Chang-Keng Chen, Taoyuan County (TW); Bing-Chen Yang, Kaohsiung (TW)

(73) Assignee: NATIONAL CHENG KUNG UNIVERSITY, Tainan (TW)

( * ) Notice: Subject to any disclaimer, the term of this patent is extended or adjusted under 35 U.S.C. 154(b) by 332 days.

(21) Appl. No.: 13/887,416

(22) Filed: May 6, 2013

(65) Prior Publication Data
US 2013/0295193 A1   Nov. 7, 2013

Related U.S. Application Data

(60) Provisional application No. 61/643,500, filed on May 7, 2012.

(51) Int. Cl.

| | | |
|---|---|---|
| *A61K 33/06* | (2006.01) | |
| *A61K 33/42* | (2006.01) | |
| *A61L 24/00* | (2006.01) | |
| *A61L 24/02* | (2006.01) | |
| *A61L 27/02* | (2006.01) | |
| *A61L 27/04* | (2006.01) | |
| *A61L 27/12* | (2006.01) | |
| *A61L 27/16* | (2006.01) | |
| *A61L 27/54* | (2006.01) | |

(52) U.S. Cl.
CPC ............. *A61L 27/04* (2013.01); *A61K 33/06* (2013.01); *A61K 33/42* (2013.01); *A61L 24/0015* (2013.01); *A61L 24/02* (2013.01); *A61L 27/02* (2013.01); *A61L 27/12* (2013.01); *A61L 27/16* (2013.01); *A61L 27/54* (2013.01); *A61L 2300/102* (2013.01); *A61L 2300/404* (2013.01); *A61L 2430/02* (2013.01); *A61L 2430/12* (2013.01)

(58) Field of Classification Search
CPC .......... A61L 27/04; A61L 27/12; A61L 27/16; A61L 27/02; A61L 27/54; A61L 24/0015; A61L 24/02; A61L 24/00; A61L 2300/102; A61L 2300/404; A61L 2430/02; A61L 2430/12; A61K 33/06; A61K 33/42

See application file for complete search history.

(56) References Cited

U.S. PATENT DOCUMENTS

| | | | | |
|---|---|---|---|---|
| 4,684,673 A | * | 8/1987 | Adachi | A61L 24/0084 523/113 |
| 5,705,273 A | * | 1/1998 | Denry et al. | 428/410 |
| 6,071,528 A | * | 6/2000 | Jensen | 424/407 |
| 2004/0266943 A1 | * | 12/2004 | Oriakhi | B28B 1/00 524/556 |
| 2009/0270527 A1 | * | 10/2009 | Lin | A61K 6/08 523/116 |
| 2010/0312355 A1 | * | 12/2010 | Yahav | A61L 27/025 623/23.61 |
| 2013/0189337 A1 | * | 7/2013 | Hashimoto | A61K 6/0017 424/401 |

FOREIGN PATENT DOCUMENTS

| | | | | |
|---|---|---|---|---|
| JP | WO 2012/046667 A1 | * | 4/2012 | ........... A61K 6/0017 |
| KR | 100957543 B1 | * | 5/2010 | |
| WO | WO 2009/007371 A1 | * | 1/2009 | |
| WO | WO 2009105614 A2 | * | 8/2009 | |

OTHER PUBLICATIONS

D. C. Smith, "Medical and Dental Applications of Cements", Journal of Biomedical Materials Research, 1971, 5(2), 189-205.*
D. Tadic and M. Epple, "A thorough physicochemical characterisation of 14 calcium phosphate-based bone substitution materials in comparison to natural bone", Biomaterials 25 (2004) 987-994.*
S. M. Barinov and V. S. Komlev, "Calcium Phosphate Bone Cements", Inorganic Materials, 2011, vol. 47, No. 13, pp. 1470-1485.*
Seung-Han Oh et al., "Preparation of calcium aluminate cement for hard tissue repair: Effects of lithium fluoride and maleic acid on setting behavior, compressive strength, and biocompatibility", Journal of Biomedical Materials Research, vol. 62, No. 4, Dec. 15, 2002, pp. 593-599, XP055180302.
Supplementary European Search Report corresponding to European Application No. EP 13787118 dated Mar. 31, 2015.

* cited by examiner

*Primary Examiner* — John Pak
*Assistant Examiner* — Nathan W Schlientz
(74) *Attorney, Agent, or Firm* — Bacon & Thomas, PLLC

(57) ABSTRACT

A preparation at least useful as a bone implant is provided, which contains a solid component including a lithium compound and a calcium compound. The preparation shows an anti-bacterial ability in comparison with a preparation contains the calcium compound but free of the lithium compound.

16 Claims, 4 Drawing Sheets

ANTIBACTERIAL CALCIUM-BASED MATERIALS

CROSS REFERENCE TO RELATED APPLICATIONS

This patent application claims the priority benefit of prior U.S. Provisional Patent Application Ser. No. 61/643,500, filed May 7, 2012.

FIELD OF THE INVENTION

The present invention is related to an anti-bacterial preparation for treating bone. More specifically, the present invention is related to an anti-bacterial preparation for treating bone which is a lithium-containing calcium-based material.

BACKGROUND OF THE INVENTION

Despite considerable research and development efforts, the problem of infections related to biomedical devices and implants persists. Bacteria evidently can readily colonize surfaces of synthetic materials, such as those used for the fabrication of catheters, hip and knee implants, dental implants, and many other devices. Infections linked to implant devices are a serious hospital problem and very often are a major cause of implant failure (Shi et al., Int J Artif Organs. 2008 September; 31(9):777-85; Zhao et al., J Biomed Mater Res B Appl Biomater. 2009 October; 91(1): 470-80; Vasilev et al., Expert Rev Med Devices. 2009 September; 6(5):553-67). As the growing colony encapsulates itself with a protective exocellular bacterial polysaccharide layer, the biofilm becomes much harder to combat than circulating bacteria (Vasilev et al., Expert Rev Med Devices. 2009 September; 6(5): 553-67). According to Ratner (UW Today Dec. 14, 1999), once the bacteria get on the device, they are extremely difficult to remove and very resistant to treatment and It can take 100 times the concentration of an antibiotic to kill the bacteria when they are attached as it takes to kill them when they're free. The reason may be a protective biofilm that bacteria produce after they become established. When that happens, often the only way to treat the infection is to remove the device from the patient. The key to stopping infections, then, lies in killing bacteria that come near the device before they form an attachment.

A number of strategies have been developed for the modification of implant or implant surface to inhibit bacterial adhesion and growth, including the incorporation of Na, K and Cl compounds (Mari'a et al., 2012; Uwe et al., 2005), nitric oxide (Nablo B J et al., 2005), antibiotics such as gentamicin, cephalothin, carbenicillin, amoxicillin, cefamandol, tobramycin and vancomycin (Stallmann H P et al., 2006; Stallmann H P et al., 2006; Bohner M et al., 2000; Zhao L et al., 2009; Zhao L et al., 2009; Akif et al., 2008; Helen et al., 2010; A. Dion et al., 2005), silver and chitosan nanoparticles (Huiliang et al., 2010; Volker et al., 2003; Ewald A et al., 2011; Shi Z et al., 2006), $TiO_2$ (Lingzhou et al., 2011; Bogdan et al., 2009), ion implanted copper and silver (N. Matsumoto et al., 2009; Jayesh et al., 2008), etc., and a number of review articles have been published (Vasilev et al., Expert Rev Med Devices. 2009 September; 6(5): 553-67; Cao and Liu, Wiley Interdiscip Rev Nanomed Nanobiotechnol. 2010 November-December; 2(6): 670-84; Chaloupka et al., Trends Biotechnol. 2010 November; 28(11):580-8. Epub 2010 Aug. 18). The proposed antibacterial implants include polymeric systems (Alt et al, Biomaterials Volume 25, Issue 18, August 2004, Pages 4383-4391; Shi et al., Biomaterials Volume 27, Issue 11, April 2006, Pages 2440-2449; Marks et al., The Journal of Bone and Joint Surgery. American Volume 1976, 58(3): 358-64), metallic systems (Visai et al., Int J Artif Organs. 2011 September; 34(9): 929-46; Heidenau et al., J Mater Sci Mater Med. 2005 October; 16(10): 883-8; Fiedler et al., Int J Artif Organs. 2011 September; 34(9): 882-8; Cao et al., Biomaterials. 2011 January; 32(3):693-705), Kazemzadeh-Narbat M et al., 2010; Yoshinari M et al., 2001; Yoshinari M et al., 2010), and ceramic systems (Gbureck et al., Biomaterials. 2005 December; 26(34):6880-6; Kim et al., 2007, Key Engineering Materials, 330-332, 791; Bohner et al., Journal of Pharmaceutical Sciences Volume 86, Issue 5, pages 565-572, May 1997).

SUMMARY OF THE INVENTION

A primary objective of the present invention is to provide anti-bacterial preparation for treating a bone.

Further, the present invention is also aimed to provide a process for preparing the anti-bacterial preparation, and a method of using the anti-bacterial preparation in treating a bone.

The anti-bacterial preparation provided according to the present invention comprises a solid component comprising a lithium compound and a calcium compound, wherein the anti-bacterial preparation shows an improved anti-bacterial ability in comparison with a preparation containing the calcium compound but free of the lithium compound.

A Hanks' solution with the anti-bacterial preparation of the present invention immersed therein with a ratio of solution:anti-bacterial preparation=10 cc/g exhibits a pH value of not less 10.

Preferably, the anti-bacterial preparation contains about 5-80%, more preferably about 10-70% of the lithium compound, based on the weight of the solid component.

Preferably, the lithium compound is a lithium salt, lithium oxide, lithium amide ($LiNH_2$), lithium hydroxide or lithium halide; and more preferably lithium carbonate, lithium sulfate, lithium phosphate, lithium oxide, lithium fluoride, lithium acetate, lithium bromide, lithium hydroxide, lithium nitrate, lithium nitrite, lithium iodide, lithium molybdate ($Li_2MoO_4$), lithium tetraborate ($Li_2B_4O_7$), lithium citrate tetrahydrate ($Li_3C_6H_5O_7.4H_2O$), or lithium stearate ($LiC_{18}H_{35}O_2$); and most preferably lithium carbonate, or lithium phosphate.

Preferably, the solid component is a powder component comprising the lithium compound and the calcium compound, wherein the calcium compound is selected from the group consisting of a calcium phosphate, calcium sulfate, calcium oxide, calcium carbonate, calcium hydroxide, calcium magnesium phosphate, calcium nitrate, calcium citrate, calcium chloride and a mixture thereof; and more preferably the calcium compound is a calcium sulfate, a calcium phosphate source, or a mixture thereof. Preferably, the calcium phosphate is tetracalcium phosphate (TTCP), dicalcium phosphate, tricalcium phosphate, monocalcium phosphate or a mixture thereof. Preferably, the calcium sulfate is calcium sulfate hemihydrate (CSH), calcium sulfate dehydrate (CSD), anhydrous calcium sulfate, or a mixture thereof.

Preferably, the anti-bacterial preparation further comprises a setting liquid component with a liquid to powder ratio of 0.20 ml/g to 0.80 ml/g, when the solid component is the powder component.

The present invention also provides a method for treating a subject comprising forming a bone cement paste by mixing the powder component and the setting liquid component of the anti-bacterial preparation of the present invention; and filling a hole or cavity in a bone with said bone cement paste which sets hard in the hole or cavity in need of said treatment.

Preferably, the solid component is a block, or granules or pieces obtained by breaking up said block. The block comprises the lithium compound and the calcium compound, wherein the calcium compound is selected from the group consisting of calcium phosphate, calcium sulfate, calcium oxide, calcium carbonate, calcium hydroxide, calcium magnesium phosphate, hydroxyapitite, or a mixture thereof, and preferably is selected from the group consisting of tetracalcium phosphate, dicalcium phosphate, hydroxyapitite, calcium sulfate dihydrate, calcium sulfate hemihydrate, or a mixture thereof.

The present invention also provides a method for treating a subject comprising implanting said block, said granules or said pieces of the anti-bacterial preparation of the present invention in said subject in need of said treatment.

Preferably, the anti-bacterial preparation further comprises a lithium retarding agent which slows down the lithium compound releasing from said anti-bacterial preparation. More preferably, the lithium retarding agent is poly(acrylic acid). Preferably, the anti-bacterial preparation comprises, based on the total weight of the anti-bacterial preparation, 0.01-5% of poly(acrylic acid) having a repeating unit of —(CH$_2$—C(COOH)H)$_n$—, wherein n=50-50000, preferably 1000-5000, and more preferably 1500-2500.

MAJOR ADVANTAGES OF THE PRESENT INVENTION (a) The inventive antibacterial agent (lithium compound) is not an antibiotic and thus is free from all kinds of antibiotic-related side effects.

(b) The inventive antibacterial lithium compound can gradually dissolve from an implant after it is implanted, keeping bacteria from approaching the implant. Furthermore, the dissolution rate of the antibacterial lithium compound can be adjusted to avoid its concentration being too high, causing negative response of the surrounding tissues, or being too low, causing insufficient antibacterial effect.

(c) The effective antibacterial duration can be adjusted to avoid being too long or too short. Unlike those implant devices incorporating permanent antibacterial agents such as metallic antibacterial agents, the duration of the present inventive antibacterial preparation can be so designed that, at the end of the desired antibacterial duration (the majority of antibacterial agent has been released), the biocompatibility of the implant will readily increase to a normal, acceptable level.

(d) After the inventive antibacterial lithium compound dissolves, pores of designed sizes are formed that enhance bioresorption rate of the implant by allowing surrounding bone cells to grow into the pores.

DETAILED DESCRIPTION OF THE INVENTION

Figure 1:
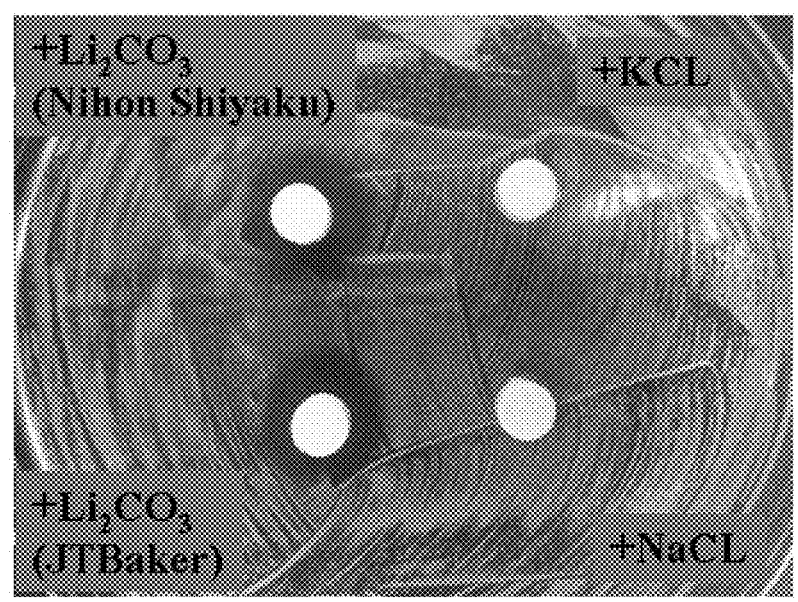
FIG. 1 shows antibacterial zones of TTCP/DCPA/CSH/Li samples prepared according to the present invention and TTCP/DCPA/CSH/alkaline metal salt samples.
Figure 2:
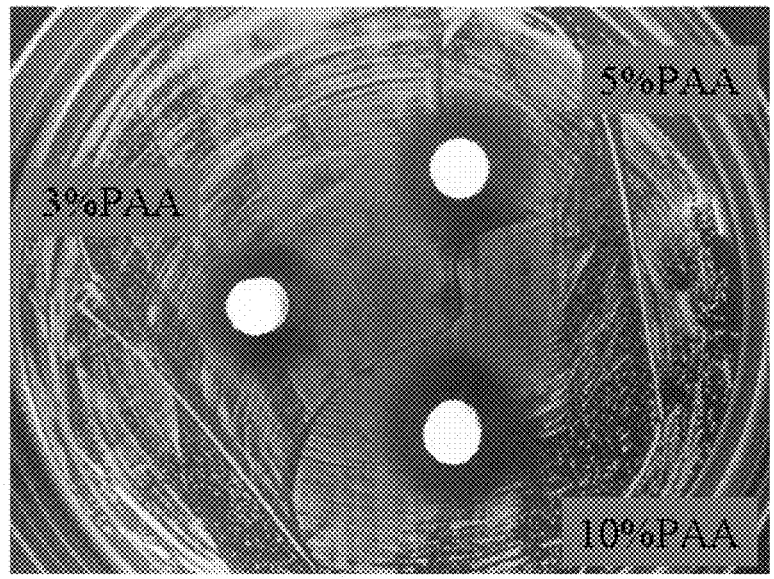
FIGS. 2 to 5 show antibacterial zones of TTCP/DCPA/CSH/Li/PAA blocks prepared according to the present invention immersed in Hanks' solution for one, two, three and five days, respectively.
Figure 3:
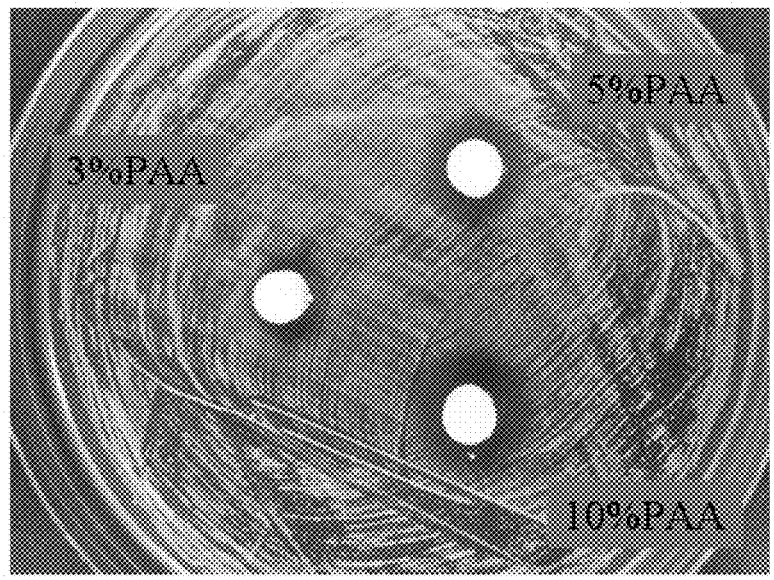
Figure 4:
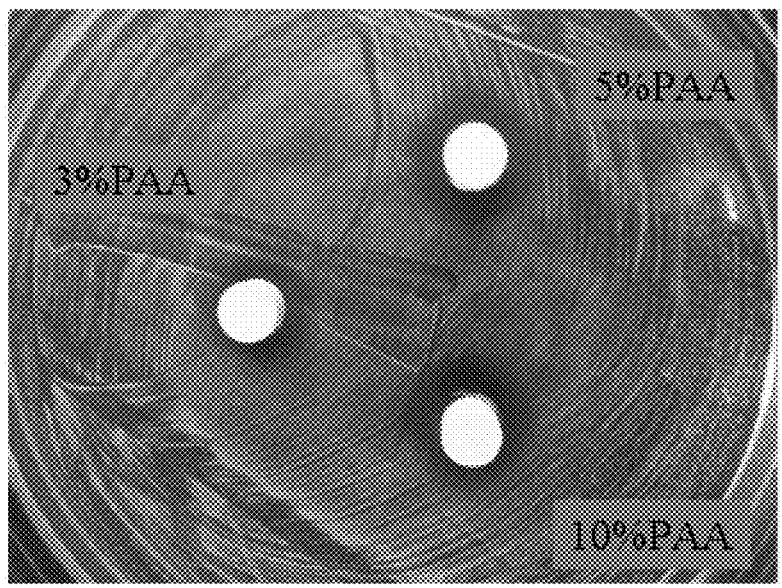
Figure 5:
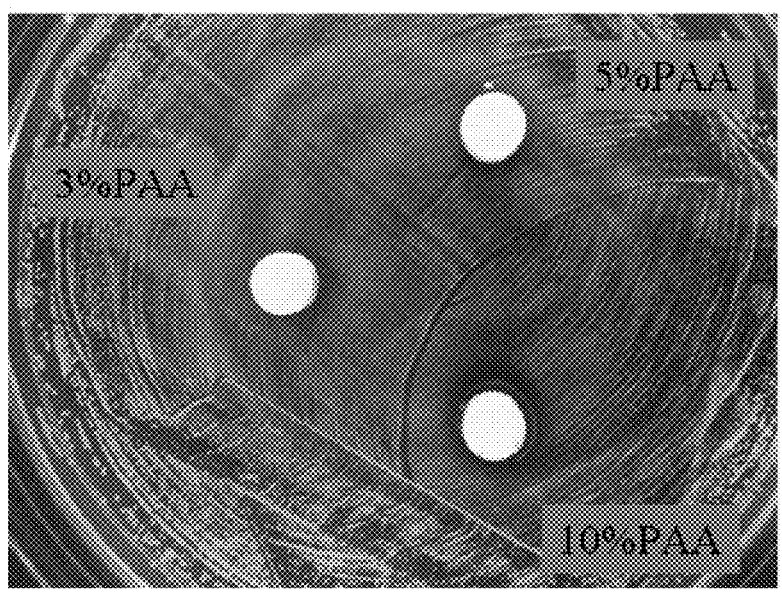

Preferred embodiments of the present invention include but not limited to the following items:
1. An anti-bacterial formula for treating a bony site comprising a calcium (Ca) source and a lithium (Li) source.
2. The anti-bacterial formula of Item 1 contains about 5-80%, more preferably about 10-70% of the lithium source, based on the weight of the calcium source and the lithium source.
3. The lithium source in Item 1 is selected from the group consisting of lithium carbonate, lithium sulfate, lithium phosphate, lithium oxide, lithium fluoride, lithium acetate, lithium bromide, lithium hydroxide, lithium nitrate, lithium nitrite, lithium iodide, lithium molybdate (Li$_2$MoO$_4$), lithium amide (LiNH$_2$), lithium tetraborate (Li$_2$B$_4$O$_7$), lithium citrate tetrahydrate (Li$_3$C$_6$H$_5$O$_7$.4H$_2$O), lithium stearate (LiC$_{18}$H$_{35}$O$_2$).
4. The lithium source in Item 2 is lithium carbonate and/or lithium phosphate.
5. The calcium source in Item 1 is calcium phosphate, calcium sulfate, calcium oxide, calcium carbonate, calcium hydroxide, calcium magnesium phosphate, calcium nitrate, calcium citrate, calcium chloride, or a mixture thereof.
6. The calcium phosphate in Item 5 is tetracalcium phosphate (TTCP), dicalcium phosphate, tricalcium phosphate (TCP), hydroxyapatite (HA), or a mixture thereof.
7. The dicalcium phosphate in Item 6 is dicalcium phosphate anhdydrous (DCPA).
8. The calcium sulfate in Item 5 is calcium sulfate hemihydrate (CSH), calcium sulfate dihydrate (CSD), anhydrous calcium sulfate, or a mixture thereof.
9. The calcium source in Item 5 comprises calcium phosphate and calcium sulfate.
10. The calcium phosphate in Item 9 comprises tetracalcium phosphate (TTCP).
11. The calcium phosphate in Item 10 further comprises dicalcium phosphate.
12. The dicalcium phosphate in Item 11 is dicalcium phosphate anhdydrous (DCPA).
13. The calcium sulfate in Item 9 comprises calcium sulfate hemihydrate (CSH).
14. The anti-bacterial formula in Item 1 further comprises a lithium retarding agent which can slow down lithium release from said anti-bacterial formula.
15. The lithium retarding agent in Item 14 is poly(acrylic acid) (PAA).
16. The anti-bacterial formula in Item 15 comprises, based on the total weight of the anti-bacterial preparation, 0.01-5% of poly(acrylic acid) having a repeating unit of —(CH$_2$—C(COOH)H)$_n$—, wherein n=50-50000, preferably 1000-5000, and more preferably 1500-2500.
17. The anti-bacterial formula in Item 1 further comprises a pore-forming agent, thereby pores form in vivo after dissolution of said pore-forming agent.
18. The pore-forming agent in Item 17 is selected from the group consisting of LiCl, KCl, NaCl, MgCl$_2$, CaCl$_2$, NaIO$_3$, KI, Na$_3$PO$_4$, K$_3$PO$_4$, Na$_2$CO$_3$, amino acid-sodium salt, amino acid-potassium salt, glucose, polysaccharide, fatty acid-sodium salt, fatty acid-potassium salt, potassium bitartrate (KHC$_4$H$_4$O$_6$), potassium carbonate, potassium gluconate ($KC_6H_{11}O_7$), potassium-sodium tartrate ($KNaC_4H_4O_6 \cdot 4H_2O$), potassium sulfate ($K_2SO_4$), sodium sulfate, sodium lactate and mannitol.

19. The pore-forming agent in Item 18 is about 10-80% in volume, preferably about 20-60% in volume, based on the volume of the calcium source and the lithium source.

20. The anti-bacterial formula in Item 1 is in powder form, cement form, dense block (pre-molded) form, dense granule form, porous block (pre-molded) form, porous granule form, or a mixture thereof.

21. The anti-bacterial formula in cement form in Item 20 further comprises a setting liquid agent, thereby mixing said calcium source, said lithium source, and said setting liquid agent, a cement paste can be formed.

22. The setting liquid agent in Item 21 comprises ammonium ion ($NH_4^+$) in a concentration of about 0.01 M to about 2 M.

23. The setting liquid agent in Item 22 is a solution of $NH_4H_2PO_4$, $(NH_4)_2HPO_4$, $(NH_4)_3PO_4 \cdot 3H_2O$, $(NH_4)_3PO_4$, or a mixture thereof.

24. The setting liquid agent in Item 23 is a solution of $(NH_4)_2HPO_4$.

25. The liquid-to-powder ratio in Item 24 is about 0.1 cc/g to about 1.0 cc/g, preferably about 0.2 cc/g to about 0.8 cc/g.

26. The anti-bacterial formula in dense block (pre-molded) form in Item 20 is prepared by a method comprising preparing a cement paste by mixing a cement powder and a setting liquid agent in Item 21; shaping the paste in a mold; and removing the mold to form a dense block.

27. The method in Item 26 further comprises pressurizing said paste in said mold before said paste becomes set to remove a portion of liquid from said paste, so that a liquid-to-powder ratio of said paste decreases, wherein the pressure applied to the paste in the mold is from about 1 MPa to 500 MPa, preferably from 100 MPa to 500 MPa.

28. The method in Item 26 further comprises impregnating the dense block with an impregnating liquid for a period of time, so that a compressive strength of the resulting impregnated block removed from the impregnating liquid is increased compared to that of said block without said impregnating treatment.

29. The impregnating liquid in Item 28 is a phosphate-containing solution having a phosphate concentration from about 0.1M to about 3M.

30. The anti-bacterial formula in dense granule form in Item 20 is prepared by a method comprising preparing a cement paste by mixing a cement powder and a setting liquid agent in Item 21; shaping the paste in a mold; removing the mold to form a dense block; and crushing said dense block into dense granules.

31. The method in Item 30 further comprises pressurizing said paste in said mold before said paste becomes set to remove a portion of liquid from said paste, so that a liquid-to-powder ratio of said paste decreases, wherein the pressure applied to the paste in the mold is from about 1 MPa to 500 MPa, preferably from 100 MPa to 500 MPa.

32. The method in Item 30 further comprises impregnating the dense granules with an impregnating liquid for a period of time, so that a compressive strength of the resulting impregnated dense granules removed from the impregnating liquid is increased compared to that of said granules without said impregnating treatment.

33. The impregnating liquid in Item 32 is a phosphate-containing solution having a phosphate concentration from about 0.1M to about 3M.

34. The anti-bacterial formula in porous block form in Item 20 is prepared by a method comprising preparing a cement paste by mixing a cement powder and a setting liquid agent in Item (21), wherein a pore-forming agent is added into the cement; shaping the paste in a mold; removing the mold to form a block article; and immersing said block article in an immersing liquid to dissolve at least a portion of said pore-forming agent in the immersing liquid, creating pores therein, so that a porous block is formed, and preferably the porous block has a porosity of 50-90 vol %.

35. The method in Item 34 further comprises pressurizing said paste in said mold before said paste becomes set to remove a portion of liquid from said paste, so that a liquid-to-powder ratio of said paste decreases, wherein the pressure applied to the paste in the mold is from about 1 MPa to 500 MPa, preferably from 100 MPa to 500 MPa.

36. The method in Item 34 further comprises impregnating the porous block with an impregnating liquid for a period of time, so that a compressive strength of the resulting impregnated porous block removed from the impregnating liquid is increased compared to that of said porous block without said impregnating treatment.

37. The impregnating liquid in Item 36 is a phosphate-containing solution having a phosphate concentration from about 0.1M to about 3M.

38. The anti-bacterial formula in porous granule form in Item 20 is prepared by a method comprising preparing a cement paste by mixing a cement powder and a setting liquid agent in Item 21, wherein a pore-forming agent is added into the cement; shaping the paste in a mold; removing the mold to form a block article; immersing said block article in an immersing liquid to dissolve at least a portion of said pore-forming agent in the immersing liquid, creating pores therein, so that a porous block is formed, and preferably the porous block has a porosity of 50-90 vol %; and crushing said porous block into porous granules.

39. The anti-bacterial formula in porous granule form in Item 20 is prepared by a method comprising preparing a cement paste by mixing a cement powder and a setting liquid agent in Item 21, wherein a pore-forming agent is added into the cement; shaping the paste in a mold; removing the mold to form a dense block article; crushing said dense block article into dense granules; and immersing said dense granules in an immersing liquid to dissolve at least a portion of said pore-forming agent in the immersing liquid, creating pores therein, so that porous granules are formed, and preferably the porous granules have a porosity of 50-90 vol %.

40. The methods in Items 38 or 39 further comprise pressurizing said paste in said mold before said paste becomes set to remove a portion of liquid from said paste, so that a liquid-to-powder ratio of said paste decreases, wherein the pressure applied to the paste in the mold is from about 1 MPa to 500 MPa, preferably from 100 MPa to 500 MPa.

41. The methods in Item 38 or 39 further comprise impregnating the porous block with an impregnating liquid for a period of time, so that a compressive strength of the resulting impregnated porous granules removed from the impregnating liquid is increased compared to that of said porous granules without said impregnating treatment.

42. The impregnating liquid in Item 41 is a phosphate-containing solution having a phosphate concentration from about 0.1M to about 3M.

43. The pore-forming agent in Items 34 or 38 is selected from the group consisting of LiCl, KCl, NaCl, $MgCl_2$, $CaCl_2$, $NaIO_3$, KI, $Na_3PO_4$, $K_3PO_4$, $Na_2CO_3$, amino acid-sodium salt, amino acid-potassium salt, glucose, polysaccharide, fatty acid-sodium salt, fatty acid-potassium salt, potassium bitartrate ($KHC_4H_4O_6$), potassium carbonate, potassium gluconate ($KC_6H_{11}O_7$), potassium-sodium tartrate ($KNaC_4H_4O_6 \cdot 4H_2O$), potassium sulfate ($K_2SO_4$), sodium sulfate, sodium lactate and mannitol.

44. The anti-bacterial formula in Item 1 further comprises a growth factor, a BMP, living cells, or a drug.
45. The bony site in Item 1 is an orthopedic site or a dental site.
46. The orthopedic site or dental site in Item 45 is a fractured site, a diseased site, or an infected site.
47. The diseased site in Item 46 is a gum-diseased site.
48. The bony site in (1), wherein a pH value is increased to at least 10 when at least a portion of said anti-bacterial formula is dissolved at said site.

EXPERIMENTAL PROCEDURES

Abbreviation

TTCP: tetracalcium phosphate
DCPA: dicalcium phosphate anhydrous
CSH: calcium sulfate hemihydrate
PAA: poly(acrylic acid)
L/P ratio: liquid/powder ratio

TABLE 1

Chemicals used for the study

| Chemical | Formula | Manufacturer | Location |
|---|---|---|---|
| Dicalcium pyrophosphate | $Ca_2P_2O_7$ | Alfa | USA |
| Tetracalcium phosphate (TTCP) | $Ca_4(PO_4)_2O$ | Fabricated in-house | Taiwan |
| Dicalcium phosphate anhydrous (DCPA) | $CaHPO_4$ | ACROS and Innophos | New jersey, USA |
| Calcium sulfate hemihydrate (CSH) | $CaSO_4 \cdot \frac{1}{2}H_2O$ | Showa | Tokyo, Japan |
| Diammonium hydrogen phosphate | $(NH_4)_2HPO_4$ | Showa | Tokyo, Japan |
| Calcium carbonate | $CaCO_3$ | Katayama | Japan |
| Lithium sulfate | $Li_2SO_4$ (99% purity) | Nihon Shiyaku Industries | Osaka, Japan |
| Lithium phosphate | $Li_3PO_4$ (99% purity) | Nihon Shiyaku Industries | Osaka, Japan |
| Lithium carbonate | $Li_2CO_3$ (99% purity) | Nihon Shiyaku Industries | Osaka, Japan |
| Lithium carbonate | | JT Baker | |
| Lithium oxide | $Li_2O$ (99% purity) | Alfa | USA |
| Lithium fluoride | LiF (98% purity) | Nihon Shiyaku Industries | Osaka, Japan |
| Poly(acrylic acid) (PAA) | —$(CH_2$—$C(COOH)H)n$ | Showa | Tokyo, Japan |

Preparation of TTCP, TTCP/DCPA, TTCP/CSH and TTCP/DCPA/CSH Powders

The TTCP powder was fabricated in-house from the reaction of dicalcium pyrophosphate ($Ca_2P_2O_7$) (Alfa, USA) and calcium carbonate ($CaCO_3$) (Katayama Chem. Co., Tokyo, Japan) using the method suggested by Brown and Epstein [Journal of Research of the National Bureau of Standards—A Physics and Chemistry 6 (1965) 69A 12].

TTCP powder was prepared by mixing $Ca_2P_2O_7$ powder with $CaCO_3$ powder uniformly for 12 hours. The mixing ratio of $Ca_2P_2O_7$ powder to $CaCO_3$ powder was 1:1.27 (weight ratio) and the powder mixture was heated to 1400° C. to allow two powders to react to form TTCP.

Appropriate amounts of TTCP and DCPA powders were uniformly mixed in a ball miller in a molar ratio of 1:1 to obtain a TTCP/DCPA mixed powder. Appropriate amounts of TTCP and CSH powders were uniformly mixed in a ball miller to obtain a TTCP/CSH mixed powder. Appropriate amounts of the TTCP/DCPA mixed powder (in a molar ratio of 1:1) and CSH powder were uniformly mixed in a ball miller to obtain a TTCP/DCPA/CSH mixed powder.

Preparation of TTCP/Li Compound, TTCP/DCPA/Li Compound, TTCP/CSH/Li Compound and TTCP/DCPA/CSH/Li Compound Mixed Powders Appropriate amounts of Li compound(s) (for example, lithium carbonate, lithium phosphate, lithium sulfate, or lithium oxide) and TTCP, TTCP/DCPA, TTCP/CSH or TTCP/DCPA/CSH were uniformly mixed in a ball miller to obtain a TTCP/Li compound, TTCP/DCPA/Li compound, TTCP/CSH/Li compound or TTCP/DCPA/CSH/Li compound mixed powder.

Preparation of PAA-Containing Setting Solutions $(NH_4)_2HPO_4$ solutions with and without PAA addition were both used as setting solution and their effects on the antibacterial behavior of various Li-containing samples were compared. The poly(acrylic acid) (abbreviated as PAA) used in this study has a molecular weight of 150,000 and was obtained as 25 wt % aqueous solution (reagent grade, Showa, Japan). PAA-containing $(NH_4)_2HPO_4$ setting solutions of different concentrations were prepared by adding different volume percentages of the PAA aqueous solution into the $(NH_4)_2HPO_4$ solutions.

Preparation of TTCP/Li Compound, TTCP/DCPA/Li Compound, TTCP/CSH/Li Compound and TTCP/DCPA/CSH/Li Compound Cement Pastes with and without PAA A series of TTCP/Li compound, TTCP/DCPA/Li compound, TTCP/CSH/Li compound and TTCP/DCPA/CSH/Li compound cement pastes with and without PAA were respectively prepared by mixing appropriate amounts of each mixed powders and $(NH_4)_2HPO_4$ setting solutions with and without PAA addition at appropriate L/P ratios.

Working Time/Setting Time Measurement of the Cement Pastes

The working time of cement paste was determined by the time after that the cement paste was no longer workable. The setting time of cement paste was measured according to the standard method set forth in ISO 1566 for dental zinc phosphate cements. The cement is considered set when a 400 gm weight loaded onto a Vicat needle with a 1 mm diameter tip fails to make a perceptible circular indentation on the surface of the cement.

Preparation of TTCP/Li Compound, TTCP/DCPA/Li Compound, TTCP/CSH/Li Compound and TTCP/DCPA/CSH/Li Compound Blocks and Granules with and without PAA Appropriate amounts of TTCP/Li compound, TTCP/DCPA/Li compound, TTCP/CSH/Li compound or TTCP/DCPA/CSH/Li compound mixed powder were mixed with $(NH_4)_2HPO_4$ setting solution with or without PAA with a desirable L/P ratio to form a cement paste.

Prior to being fully hardened, the paste was placed in a mold under a desirable pressure (e.g., 450 Kgf or 156 MPa) to squeeze a portion of the liquid out of the paste. After being removed from the mold, optionally, some block samples were further impregnated in an impregnation solution (for example, 1-3 M $(NH_4)_2HPO_4$ or $K_2HPO_4$) at a desirable temperature (for example, 0-50° C.) for a desirable period of time (for example, 1 day) to increase strength, followed by drying in an oven (for example, at 50° C. for 1 day). Optionally the block was crushed into granules with a desirable particle size distribution range. Optionally, the mold can be tailor-made to produce a block with a desirable shape and geometry.

Immersion, pH and Weight Loss Measurements

Various Li-containing samples were immersed in Hanks' solution (with a pH value of 7.4) with a solution/sample ratio of 10 cc/g for different periods of time (1 d, 2 d, 3 d, 5 d and 7 d). Their immersion-induced weight losses and pH changes in the solution were determined. The Hanks' solution was refreshed daily during immersion test to help maintain uniform ion concentrations of the solution. The pH values of the solution were measured using a pH meter (Suntex Instruments SP2300, Taipei, Taiwan).

Cytotoxicity Test

The cytotoxicity test was performed according to ISO 10993-5. The extraction method was used. NIH/3T3 fibroblasts (seeding density 5000 per well) were pre-cultured for 24 h in Dulbecco's modified essential medium (DMEM) supplemented with bovine serum (10%) and PSF (1%). An extract was prepared by immersing a hardened cement paste in the culture medium at a ratio of 0.1 (g/ml) at 37° C. for 24 h and then collecting the liquid by centrifugation. The extract was added to the 96 well microplate (100 µl per well) incubated in a 5% $CO_2$ humidified atmosphere at 37° C. After 24 h, the extract was sucked out and then a mixture of the culture medium (100 µl) and WST-1 (10 µl) was added to the wells and incubated for 1 h at 37° C. Cell viability was measured by using the WST-1 assay. This is a colorimetric assay of mitochondrial dehydrogenase activity where the absorbance at 450 nm is proportional to the amount of dehydrogenase activity in the cell. After 1 h incubation, the mixture of medium and WST-1 was transferred to a 96 well microplate and the absorbance at 450 nm was measured with an ELISA reader. $Al_2O_3$ powder was also assayed as a control. Four bars were tested for each sample (n=4).

TABLE 2

| Cell line used for cytotoxicity test | |
|---|---|
| Cell name | NIH/3T3 |
| Cell number | BCRC 60008 |
| Type | Mouse NIH/Swiss embryo |
| Growth property | Adherent, 5% $CO_2$, 37° C. |
| Morphology | Fibroblast |
| Cell culture medium | 90% Dulbecco's modified Eagle's medium (DMEM) + 10% bovine serum |
| Freeze medium | 93% culture medium + 7% DMSO |

Antibacterial Testing

Preparation of Tryptic Soy Broth (TSB) Medium

To prepare a TSB medium, 6 g Tryptone (Neogen, USA), 2 g Soytone (Soytone BD, USA) and 2 g NaCl (J.T. Baker, USA) were placed into a beaker filled with 400 ml of double distilled water and mixed with a stir bar. After total dissolution, the pH of the solution was adjusted to 7.3 and the solution was autoclaved (121° C., 1.2 kg/cm$^2$) for 30 min.

Preparation of Tryptic Soy Agar (TSA) Medium

To prepare a TSA medium, 6 g Tryptone (Neogen, USA), 2 g Soytone (Soytone BD, USA), 2 g NaCl (J.T. Baker, USA) and 6 g Agar (Neogen, USA) were placed into a beaker filled with 400 ml of double distilled water and mixed with a stir bar. After total dissolution, the pH of the solution was adjusted to 7.3 and the solution was autoclaved (121° C., 1.2 kg/cm$^2$) for 30 min. After being sterilized, the TSA medium was poured into a petri dish and allowed hardened. The TSA medium was then placed into an incubator at 30° C.

Disk Diffusion Assay 1 ml staphylococcus aureus (SA) containing TSB medium was transferred into a 15 ml centrifuge tube, wherein 10 ml phosphate buffered saline (PBS) was added and mixed gently. The mixture was centrifuged (KUBOTA 5922, Japan) at 3000 rpm for 10 minutes. The supernatant was removed and a SA pellet remained. 1 ml PBS was then added to suspend the pellet. 20 µl of the SA suspension and 180 µl PBS were transferred into each well of a 96 well plate. The absorbance was assayed using an ELISA reader (Sunrise, Tecan, Switzerland) at 600 nm to determine the bacterial concentration (cfu/ml) (200 µl of PBS was used as a negative control). Once determined, an appropriate volume of SA containing medium was transferred into a 1 micro centrifuge tube, wherein TSB was added to adjust bacterial concentration to $3.5 \times 10^6$ (cfu/ml). The tube was shaked for 15 seconds to allow thorough mixing. 100 µl of the SA containing medium was removed and dropped evenly across the agar plate. Once the broth was distributed evenly on agar plate and became almost dry, samples to be tested were placed on top of the agar and the petri dish was covered with a parafilm. The dish was placed in an incubator (LM-570R, Yih Der, Taiwan) at 37° C. for 24 hours. Bacteria colony formation was then observed and colony diameters measured.

Soaking in Hanks' Solution

After being loaded, the samples were placed on a table for 1 hour to become dry. Four samples were then placed into a 20 ml glass vial, wherein 8 ml Hanks' solution was added with a solid/liquid ratio of 0.1 g/ml. The glass vial was put into a water bath at 37° C. for 1, 2, 3, 5, and 7 days. The Hanks' solution was changed daily. Once having been soaked for desired periods of time, the samples were placed into a 50° C. oven for 24 hours, then stored in a zip lock bag.

Example 1. Antibacterial Test on Commercially Pure Lithium Salts

Antibacterial tests were conducted on a series of commercially pure lithium compounds, including $Li_2SO_4$, $Li_3PO_4$, $Li_2CO_3$, $Li_2O$, and $LiF$.

Samples were either dry-molded under a pressure of 450 kgf into a 3 mm high, 6 mm dia. cylinder without being mixed with a setting solution, or wet-molded under 1.4 MPa into a 3 mm high, 6 mm dia. cylinder with being mixed with a 0.6 M $(NH_4)_2HPO_4$ setting solution at L/P ratios 0.2-0.6 (0.20 for $Li_2SO_4$, 0.25 for $Li_3PO_4$, 0.60 for $Li_2CO_3$)

Results:
(1) All tested lithium compounds ($Li_2SO_4$, $Li_3PO_4$, $Li_2CO_3$, $Li_2O$ and $LiF$) demonstrate a high antibacterial behavior.
(2) Except $Li_2CO_3$, all dry-molded (without being mixed with a setting solution) lithium compounds are more or less disintegrated/dissolved in TSB agar plate.
(3) All wet-molded (mixed with 0.6 M $(NH_4)_2HPO_4$ at L/P=0.2-0.6 cc/g) Li compounds do not disintegrate in TSB agar plate.
(4) Wet-molded $Li_2SO_4$ and $Li_2CO_3$ samples show two largest anti-bacterial zones (22 mm and 18 mm, respectively)

Example 2. Antibacterial Behavior and Other Tests of TTCP/Li Salt and TTCP/Li Salt/PAA Samples Immersion, pH measurement, weight loss, cytotoxicity and antibacterial tests were conducted on TTCP/Li and TTCP/Li/PAA block samples.

The TTCP/Li/PAA blocks were prepared by mixing appropriate amounts of TTCP powder and $Li_2CO_3$ powder (TTCP:$Li_2CO_3$=1:1 by weight) to obtain a TTCP/$Li_2CO_3$ mixed powder. The TTCP/$Li_2CO_3$ powder was mixed with 0.6M $(NH_4)_2HPO_4$ setting solution containing 3, 5, or 10 vol % PAA solution at L/P ratio of 0.45 cc/g to obtain a TTCP/Li/PAA cement paste. The TTCP/Li/PAA block samples were prepared from pressure-molding the TTCP/Li/PAA cement paste under a pressure of 450 kgf.

TABLE 3

Average diameters (mm) of antibacterial zones of TTCP/Li/PAA blocks immersed in Hanks' solution for different periods of time (days).

|  | 1 d | 2 d | 3 d | 5 d | 7 d |
|---|---|---|---|---|---|
| 3% PAA | 11.4 | 10.3 | 8.5 | 6 | 6 |
| 5% PAA | 11.5 | 11.4 | 11.3 | 6 | 6 |
| 10% PAA | 12.6 | 12.5 | 11.7 | 6.7 | 6 |

(Note: The measured antibacterial zones include 6 mm dia. sample)

Results:
(1) The addition of PAA prolongs the antibacterial effect of the TTCP/Li formula.
(2) Sample with setting solution containing 3 vol % PAA shows an antibacterial zone of 11.4 mm after being immersed in Hanks' solution for 1 d; 10.3 mm for 2 d; 8.5 mm for 3 d.
(3) Sample with setting solution containing 5 vol % PAA shows an antibacterial zone 11.5 mm after being immersed in Hanks' solution for 1 d; 11.4 mm for 2 d; 11.2 mm for 3 d.
(4) Sample with setting solution containing 10 vol % PAA shows an anti-bacterial zone 12.6 mm after being immersed in Hanks' solution for 1 d; 12.5 mm for 2 d; 11.7 mm for 3 d; 6.7 mm for 5 d.

TABLE 4

Average pH values of Hanks' solutions wherein TTCP/Li/PAA blocks were immersed for different periods of time (days).

|  | 1 d | 2 d | 3 d | 4 d | 5 d | 6 d | 7 d | 8 d | 9 d | 10 d |
|---|---|---|---|---|---|---|---|---|---|---|
| 3% PAA | 11.4 | 12.2 | 12.0 | 11.6 | 11.2 | 10.7 | 10.6 | 10.5 | 10.4 | 10.3 |
| 5% PAA | 10.7 | 11.9 | 12.1 | 11.8 | 11.4 | 11.1 | 10.7 | 10.6 | 10.4 | 10.3 |
| 10% PAA | 10.5 | 11.0 | 11.5 | 11.9 | 11.5 | 11.1 | 10.7 | 10.6 | 10.4 | 10.3 |

Results:
(1) Average pH values of Hanks' solutions are all higher than 10, even higher than 12 in some cases.

TABLE 5

Average weight loss percentages (%) of TTCP/Li/PAA blocks immersed in Hanks' solution for different periods of time (days).

|  | 1 d | 2 d | 3 d | 5 d | 7 d | 10 d |
|---|---|---|---|---|---|---|
| 3% PAA | 11.4 | 14.9 | 17 | 23.8 | 24.4 | 27.4 |
| 5% PAA | 12.4 | 20.9 | 24.9 | 28.5 | 30.1 | 37.9 |
| 10% PAA | 15.3 | 22.5 | 28.9 | 38.6 | 39.6 | 42.8 |

Results:
(1) Average weight losses of all samples immersed in Hanks' solution increase with immersion time.
(2) The weight loss increased with PAA content.
(3) After 10 d, 27.4% of the weight is lost for 3% PAA sample; 37.9% weight is lost for 5% PAA sample; and 42.8% weight is lost for 10% PAA sample. This result is desirable, since, after the rather quick dissolution of the Li compounds, a highly porous structure is developed in the implant material that can increase the bioresorption rate of the implant.

TABLE 6

Average cell viabilities (sample/DMEM medium ratio = 0.1 g/ml, NIH-3T3) of TTCP/Li/PAA blocks immersed in Hanks' solution for different periods of time (days)

|  | 1 d | 2 d | 3 d | 5 d | 7 d | 10 d |
|---|---|---|---|---|---|---|
| 3% PAA | 39.8 | 41.2 | 42.0 | 43.2 | 43.4 | 50.0 |
| 5% PAA | 38.2 | 40.9 | 42.7 | 44.6 | 48.6 | 51.8 |
| 10% PAA | 40.8 | 42.9 | 45.1 | 44.8 | 57.4 | 75.0 |

Results:
(1) Average cell viability values of all samples immersed in Hanks' solution increase with immersion time, indicating the biocompatibility level continues to increase due to gradual consumption of the Li compound. This result is desirable, since the best result would be that, after the stage of high antibacterial effect, the implant material would gradually recover its biocompatibility level.

(2) After 7 d, the cell viability values of 10% PAA sample are significantly higher than those of 3% PAA and 5% PAA samples.

Example 3. Antibacterial Behavior and Other Tests of TTCP/DCPA/Li Salt and TTCP/DCPA/Li Salt/PAA Samples Immersion, pH measurement, weight loss, cytotoxicity and antibacterial tests were conducted on TTCP/DCPA/Li and TTCP/DCPA/Li/PAA block samples.

The TTCP/DCPA/Li blocks were prepared by mixing appropriate amounts of TTCP/DCPA powders (1:1 in molar ratio) and Li compound ($Li_2CO_3$ or $Li_2O$) powder ($Li_2CO_3$ or $Li_2O$=10 wt % or 30 wt % of all powder components) to obtain a TTCP/DCPA/Li compound mixed powder. The TTCP/DCPA/Li compound powder was mixed with 0.6 M $(NH_4)_2HPO_4$ setting solution with L/P ratio of 0.35 to obtain a TTCP/DCPA/Li cement paste. The 3 mm high, 6 mm dia. block samples were prepared from pressure-molding the cement paste under a pressure of 1.4 MPa.

TABLE 7 pH values of the PBS extract of TTCP/DCPA/Li samples immersed in 37° C. PBS for 24 h

| Sample:PBS (weight ratio) | TTCP/DCPA:$Li_2CO_3$ = 90:10 by weight | TTCP/DCPA:$Li_2CO_3$ = 70:30 by weight | TTCP/DCPA:$Li_2O$ = 90:10 by weight |
|---|---|---|---|
| 1:5 | 10.5 | 10.4 | 12.6 |
| 1:10 | 10.6 | 10.5 | 12.7 |

Results:
(1) Sample containing 90 wt % TTCP/DCPA and 10 wt % $Li_2O$ shows an anti-bacterial zone of 22 mm.
(2) Sample containing 70 wt % TTCP/DCPA and 30 wt % $Li_2CO_3$ shows an anti-bacterial zone 24 mm.
(3) The pH values of the extract are all higher than 10, even higher than 12 for $Li_2O$ sample.

The TTCP/DCPA/Li/PAA blocks were prepared by mixing appropriate amounts of TTCP/DCPA powders (1:1 in molar ratio) and $Li_2CO_3$ powder (TTCP/DCPA:$Li_2CO_3$=1:1 by weight) to obtain a TTCP/DCPA/Li mixed powder, which was then mixed with 0.6 M $(NH_4)_2HPO_4$ setting solution containing 3, 5, or 10 vol % PAA solution at L/P of 0.35 cc/g to obtain a TTCP/DCPA/Li/PAA cement paste. The 3 mm high, 6 mm dia. block samples were prepared from pressure-molding the cement paste under a pressure of 450 kgf.

TABLE 8

Average diameters (mm) of antibacterial zones of TTCP/DCPA/Li/PAA blocks immersed in Hanks' solution for different periods of time (days).

|  | 1 d | 2 d | 3 d | 5 d | 7 d |
|---|---|---|---|---|---|
| 3% PAA | 12.5 | 9.9 | 9.8 | 6 | 6 |
| 5% PAA | 12.7 | 10.6 | 10.9 | 7.3 | 6 |
| 10% PAA | 11.9 | 11.5 | 10.6 | 8.8 | 6.9 |

(Note: The measured antibacterial zones include 6 mm dia. sample)

Results:
(1) The addition of PAA prolongs the antibacterial effect of the TTCP/DCPA/Li formula.
(2) Sample with setting solution containing 3 vol % PAA shows an antibacterial zone of 12.5 mm after being immersed in Hanks' solution for 1 d; 9.9 mm for 2 d; 9.8 mm for 3 d.
(3) Sample with setting solution containing 5 vol % PAA shows an antibacterial zone 12.7 mm after being immersed in Hanks' solution for 1 d; 10.6 mm for 2 d; 10.9 mm for 3 d; 7.3 mm for 5 d.
(4) Sample with setting solution containing 10 vol % PAA shows an anti-bacterial zone 11.9 mm after being immersed in Hanks' solution for 1 d; 11.5 mm for 2 d; 10.6 mm for 3 d; 8.8 mm for 5 d; 6.9 mm for 7 d.

TABLE 9

Average pH values of Hanks' solutions wherein TTCP/DCPA/Li/PAA blocks were immersed for different periods of time (days).

|  | 1 d | 2 d | 3 d | 4 d | 5 d | 6 d | 7 d | 8 d | 9 d | 10 d |
|---|---|---|---|---|---|---|---|---|---|---|
| 3% PAA | 10.5 | 10.5 | 10.8 | 10.8 | 10.6 | 10.5 | 10.4 | — | — | — |
| 5% PAA | 10.5 | 10.7 | 10.7 | 10.7 | 10.8 | 10.6 | 10.4 | — | — | — |
| 10% PAA | 10.5 | 10.8 | 10.8 | 10.8 | 10.7 | 10.7 | 10.7 | — | — | — |

Results:
(1) Average pH values of Hanks' solution are all higher than 10.

TABLE 10

Average weight loss percentages (%) of TTCP/DCPA/Li/PAA blocks immersed in Hanks' solution for different periods of time (days).

|  | 1 d | 2 d | 3 d | 5 d | 7 d | 10 d |
|---|---|---|---|---|---|---|
| 3% PAA | 7.6 | 14 | 25.1 | 27.2 | 27.4 | — |
| 5% PAA | 8.5 | 14.3 | 26.1 | 32.1 | 33.9 | — |
| 10% PAA | 8.6 | 20.9 | 26.6 | 32.3 | 41.0 | — |

Results:
(1) Average weight losses of all samples immersed in Hanks' solution increase with immersion time.
(2) The weight loss increases with PAA content, especially after 7 d. This result is desirable, since, after the rather quick dissolution of the Li compounds, a highly porous structure is developed in the implant material that can increase the bioresorption rate of the implant.

TABLE 11

Average cell viabilities (sample/DMEM medium ratio = 0.1 g/ml, NIH-3T3) of TTCP/DCPA/Li/PAA blocks immersed in Hanks' solution for different periods of time.

|  | 1 d | 2 d | 3 d | 5 d | 7 d | 10 d |
|---|---|---|---|---|---|---|
| 3% PAA | 26.0 | 43.1 | 42.9 | — | — | 48.1 |
| 5% PAA | 25.7 | 44.0 | 43.9 | — | — | 70.6 |
| 10% PAA | 27.3 | 44.9 | 51.2 | — | — | 80.3 |

Results:
(1) Average cell viability values of all samples immersed in Hanks' solution increase with immersion time, indicating the biocompatibility level continues to increase due to gradual consumption of the Li compound. This result is desirable, since the best result would be that, after the stage of high antibacterial effect, the implant material would gradually recover its biocompatibility level.

(2) After 3 d, the cell viability values of 10% PAA sample are significantly higher than those of 3% PAA and 5% PAA samples. After 10 d, the cell viability value of 10% PAA sample reaches 80.3.

Example 4. Antibacterial Behavior of TTCP/DCPA/Li Salt/KCl Samples

Antibacterial tests were conducted on TTCP/DCPA/Li/KCl block samples. The TTCP/DCPA/Li/KCl blocks were prepared by mixing appropriate amounts of TTCP/DCPA powders (1:1 in molar ratio) and $Li_2O$ powder ($Li_2O$=10 wt % of all powder components) and further with 100-200 μm KCl powder (TTCP/DCPA/Li powder:KCL powder=60:40 by weight) to obtain a TTCP/DCPA/Li/KCl mixed powder. The mixed powder was mixed with 0.6M $(NH_4)_2HPO_4$ setting solution at L/P ratio of 0.50 cc/g to obtain a TTCP/DCPA/Li/KCl cement paste. The 3 mm high, 6 mm dia. block samples were prepared from pressure-molding the cement paste under a pressure of 450 kgf.

Results:
(1) The above-described TTCP/DCPA/Li samples show an average antibacterial zone of 21 mm.
(2) The above-described TTCP/DCPA/Li/KCl samples show an average antibacterial zone of 22 mm.

Example 5. Antibacterial Behavior and Other Tests of TTCP/CSH/Li Salt and TTCP/CSH/Li Salt/PAA Samples Immersion, pH measurement, weight loss, cytotoxicity and antibacterial tests were conducted on TTCP/CSH/Li and TTCP/CSH/Li/PAA block samples.

The TTCP/CSH/Li/PAA blocks were prepared by mixing appropriate amounts of TTCP/CSH powder (65:35 by weight) and $Li_2CO_3$ powder (TTCP/CSH:$Li_2CO_3$=1:1 by weight) to obtain a TTCP/CSH/Li mixed powder. The TTCP/CSH/Li powder was mixed with 0.6 M $(NH_4)_2HPO_4$ setting solution containing 3, 5, or 10 vol % PAA solution with L/P ratio of 0.35 to obtain a TTCP/CSH/Li/PAA cement paste. The 3 mm high, 6 mm dia. block samples were prepared from pressure-molding the cement paste under a pressure of 450 kgf.

TABLE 12

Average diameters (mm) of antibacterial zones of TTCP/CSH/Li/PAA blocks immersed in Hanks' solution for different periods of time (days).

|  | 1 d | 2 d | 3 d | 5 d | 7 d |
|---|---|---|---|---|---|
| 3% PAA | 11.7 | 8.0 | 6 | 6 | 6 |
| 5% PAA | 12.7 | 8.0 | 6 | 6 | 6 |
| 10% PAA | 13.0 | 10.0 | 11.0 | 6 | 6 |

(Note: The measured antibacterial zones include 6 mm dia. sample)

Results:
(1) The addition of PAA prolongs the antibacterial effect of the TTCP/CSH/Li formula.
(2) Sample with setting solution containing 3 vol % PAA shows an antibacterial zone of 11.7 mm after being immersed in Hanks' solution for 1 d; 8.0 mm for 2 d;
(3) Sample with setting solution containing 5 vol % PAA shows an antibacterial zone 12.7 mm after being immersed in Hanks' solution for 1 d; 8.0 mm for 2 d;
(4) Sample with setting solution containing 10 vol % PAA shows an anti-bacterial zone 13.0 mm after being immersed in Hanks' solution for 1 d; 10.0 mm for 2 d; 11.0 mm for 3 d.

TABLE 13

Average pH values of Hanks' solution wherein TTCP/CSH/Li/PAA blocks were immersed for different periods of time (days).

|  | 1 d | 2 d | 3 d | 4 d | 5 d | 6 d | 7 d | 8 d | 9 d | 10 d |
|---|---|---|---|---|---|---|---|---|---|---|
| 3% PAA | 11.9 | 12.1 | 11.5 | 11.0 | 10.8 | 10.5 | 10.5 | — | — | — |
| 5% PAA | 10.9 | 12.2 | 11.8 | 11.1 | 10.9 | 10.6 | 10.5 | — | — | — |
| 10% PAA | 10.2 | 11.5 | 12.1 | 11.6 | 11.1 | 10.7 | 10.6 | — | — | — |

Results:
(1) Average pH values of Hanks' solution are all higher than 10, even higher than 12 in some cases.

TABLE 14

Average weight loss percentages (%) of TTCP/CSH/Li/PAA blocks immersed in Hanks' solution for different periods of time (days).

|  | 1 d | 2 d | 3 d | 5 d | 7 d | 10 d |
|---|---|---|---|---|---|---|
| 3% PAA | 20.7 | 24.6 | 25.0 | 31.8 | 33.8 |  |
| 5% PAA | 18.6 | 25.9 | 30.2 | 33.3 | 37.4 |  |
| 10% PAA | 19.1 | 27.4 | 32.4 | 33.3 | 40.0 |  |

Results:
(1) Average weight losses of all samples immersed in Hanks' solution increase with immersion time.
(2) The weight loss increases with PAA content, especially after 7 d. This result is desirable, since, after the rather quick dissolution of the Li compounds, a highly porous structure is developed in the implant material that can increase the bioresorption rate of the implant.

TABLE 15

Average cell viabilities (sample/DMEM medium ratio = 0.1 g/ml, NIH-3T3) of TTCP/CSH/Li/PAA blocks immersed in Hanks' solution for different periods of time (days).

|  | 1 d | 2 d | 3 d | 5 d | 7 d | 10 d |
|---|---|---|---|---|---|---|
| 3% PAA | 38.1 | 39.7 | 40.2 | 40.7 | 50.8 | 51.9 |
| 5% PAA | 38.5 | 40.0 | 42.2 | 42.9 | 54.7 | 60.9 |
| 10% PAA | 42.2 | 42.6 | 43.1 | 43.7 | 55.1 | 76.7 |

Results:
(1) Average cell viability values of all samples immersed in Hanks' solution increase with immersion time, indicating the biocompatibility level continued to increase due to gradual consumption of the Li compound. This result is desirable, since the best result would be that, after the stage of high antibacterial effect, the implant material would gradually recover its biocompatibility level.

(2) After 10 d, the cell viability value of 10% PAA sample reaches 76.7 and is significantly higher than those of 3% PAA and 5% PAA samples.

Example 6. Antibacterial Behavior of TTCP/DCPA/CSH/Li Salt Samples

Antibacterial tests were conducted on a variety of TTCP/DCPA/CSH/Li block samples. The TTCP/DCPA/CSH/Li blocks were prepared by mixing appropriate amounts of TTCP/DCPA/CSH powder and $Li_2CO_3$ powder (TTCP/DCPA/CSH:$Li_2CO_3$=1:1 by weight) to obtain a TTCP/DCPA/CSH/Li mixed powder, wherein TTCP:DCPA=1:1 by mole and the TTCP/DCPA:CSH weight ratios are listed in Table 16. For example, the mixed powder containing 65 wt % TTCP/DCPA powder and 35 wt % CSH powder is designated "TTCP/DCPA/CSH sample 65/35" or simply "65/35"; the mixed powder containing 45 wt % TTCP/DCPA powder and 55 wt % CSH powder is designated "TTCP/DCPA/CSH sample 45/55" or simply "45/55"; and so forth.

TABLE 16

TTCP/DCPA/CSH sample designations

| TTCP/DCPA/CSH sample designation | TTCP/DCPA:CSH (by weight) | TTCP:DCPA:CSH (by weight) |
|---|---|---|
| "90/10" | 90:10 | 2.69:1:0.41 |
| "85/15" | 85:15 | 2.69:1:0.65 |
| "80/20" | 80:20 | 2.69:1:0.92 |
| "75/25" | 75:25 | 2.69:1:1.23 |
| "65/35" | 65:35 | 2.69:1:1.99 |
| "55/45" | 55:45 | 2.69:1:3.02 |
| "45/55" | 45:55 | 2.69:1:4.51 |
| "35/65" | 35:65 | 2.69:1:6.85 |
| "25/75" | 25:75 | 2.69:1:11.07 |
| "10/90" | 10:90 | 2.69:1:33.21 |

Antibacterial Behavior of TTCP/DCPA/CSH/Alkaline Metal Salt Samples

Antibacterial tests were conducted on "65/35" mixed with a series of alkaline metal salts ($Li_2CO_3$, KCl or NaCl powder), wherein "65/35": alkaline metal salt=1:1 by weight. The "65/35"/alkaline metal salt mixed powder was mixed with 0.6 M $(NH_4)_2HPO_4$ setting solution with L/P ratio of 0.35 g/cc to obtain a TTCP/DCPA/CSH/alkaline metal salt cement paste. The 3 mm high, 6 mm dia. block samples were prepared from pressure-molding the cement paste under a pressure of 450 kgf.

FIG. 1 shows the results of the antibacterial tests for the TTCP/DCPA/CSH/Li samples and TTCP/DCPA/CSH/alkaline metal salt samples.
Results of FIG. 1:
(1) Among three alkaline metal (Li, Na and K) salts tested, only Li-based alkaline metal salt ($Li_2CO_3$) shows a strong antibacterial effect with an antibacterial zone of 13 mm (for both Nihon Shiyaku and JT Baker products);
(2) No antibacterial zone was observed for samples prepared from Na salt or K salt.
Antibacterial Behavior of TTCP/DCPA/CSH/Li Samples
Antibacterial tests were conducted on "65/35" mixed with a series of different Li compounds ($Li_2SO_4$, $Li_3PO_4$, $Li_2CO_3$, $Li_2O$), wherein "65/35": Li compound=1:1 by weight. The "65/35"/Li compound mixed powder was mixed with 0.6 M $(NH_4)_2HPO_4$ setting solution with L/P ratio of 0.3-0.5 g/cc (0.3 for $Li_2SO_4$; 0.35 for $Li_3PO_4$ and $Li_2CO_3$; 0.5 for $Li_2O$) to obtain a TTCP/DCPA/CSH/Li cement paste. The 3 mm high, 6 mm dia. block samples were prepared from pressure-molding the cement paste under a pressure of 450 kgf.
Results:
(1) Sample containing $Li_2O$ shows the strongest antibacterial effect, although it was disintegrated in TSB agar plate.
(2) Samples containing $Li_2O$ and $Li_2CO_3$ show stronger antibacterial effect than those containing $Li_2SO_4$ or $Li_3PO_4$.
Antibacterial Behavior of TTCP/DCPA/CSH/Li Salt Samples
Antibacterial tests were conducted on "55/45" mixed with $Li_2CO_3$ powder, wherein "55/45": $Li_2CO_3$=1:1 or 7:3 by weight. The "55/45"/$Li_2CO_3$ powder was mixed with 0.6 M $(NH_4)_2HPO_4$ setting solution with L/P ratio of 0.35 g/cc to obtain a TTCP/DCPA/CSH/Li salt cement paste. The 3 mm high, 6 mm dia. block samples were prepared from pressure-molding the cement paste under a pressure of 1.4 MPa.
Results:
(1) Sample containing 70 wt % "55/45" and 30 wt % $Li_2CO_3$ shows an antibacterial zone of 13 mm;
(2) Sample containing 50 wt % "55/45" and 50 wt % $Li_2CO_3$ shows an antibacterial zone of 17 mm.
Antibacterial Behavior of TTCP/DCPA/CSH/Li Salt Samples
Antibacterial tests were conducted on "65/35" mixed with $Li_2CO_3$, wherein "65/35": $Li_2CO_3$=7:3 by weight. The "65/35"/$Li_2CO_3$ powder was mixed with 0.6 M $(NH_4)_2HPO_4$ setting solution with L/P ratio of 0.35 g/cc to obtain a TTCP/DCPA/CSH/Li salt cement paste. The 3 mm high, 6 mm dia. block samples were prepared from pressure-molding the cement paste under a pressure of 450 kgf. The TTCP/DCPA/CSH/Li salt block samples were subsequently heated to 400° C. for 1 h or 2 h.
Results:
(1) TTCP/DCPA/CSH/Li salt block sample heated to 400° C. for 1 h shows an antibacterial zone of 15 mm;
(2) TTCP/DCPA/CSH/Li salt block sample heated to 400° C. for 2 h shows an antibacterial zone of 16 mm.

Example 7. Antibacterial Behavior and Other Tests of TTCP/DCPA/CSH/Li Salt/PAA Samples Immersion, pH measurement, weight loss, cytotoxicity and antibacterial tests were conducted on a variety of TTCP/DCPA/CSH/Li/PAA block samples. The TTCP/DCPA/CSH/Li/PAA blocks were prepared by mixing appropriate amounts of TTCP/DCPA/CSH powder and $Li_2CO_3$ powder with a desired TTCP/DCPA/CSH:$Li_2CO_3$ weight ratio (for example 1:1 by weight) to obtain a TTCP/DCPA/CSH/Li mixed powder, wherein TTCP:DCPA=1:1 by mole and the TTCP/DCPA:CSH weight ratios are listed in Table 16. For example, the mixed powder containing 65 wt % TTCP/DCPA powder and 35 wt % CSH powder is designated "TTCP/DCPA/CSH sample 65/35" or simply "65/35"; the mixed powder containing 45 wt % TTCP/DCPA powder and 55 wt % CSH powder is designated "TTCP/DCPA/CSH sample 45/55" or simply "45/55"; and so forth.
Antibacterial Tests of TTCP/DCPA/CSH/Li Salt/PAA Samples
"65/35" powder (TTCP/DCPA:CSH=65:35 by weight) is mixed with $Li_2CO_3$ powder ("65/35": $Li_2CO_3$=70:30 by weight) to obtain a TTCP/DCPA/CSH/Li mixed powder. The resulting TTCP/DCPA/CSH/Li powder was mixed with 0.6 M $(NH_4)_2HPO_4$ setting solution containing 3 vol % PAA solution with L/P ratio of 0.35 cc/g to obtain a TTCP/DCPA/CSH/Li/PAA cement paste. The 3 mm high, 6 mm dia. block samples were prepared from pressure-molding the cement paste under a pressure of 450 kgf.

Results:
(1) 3% PAA sample shows an anti-bacterial zone 15 mm.

Antibacterial and Other Tests of TTCP/DCPA/CSH/Li Salt/PAA Samples

The TTCP/DCPA/CSH/Li/PAA blocks were prepared by mixing appropriate amounts of "65/35" powder and $Li_2CO_3$ powder ("65/35": $Li_2CO_3$=1:1 by weight) to obtain a TTCP/DCPA/CSH/Li mixed powder, wherein TTCP:DCPA=1:1 by mole and TTCP/DCPA:CSH=65:35 by weight. The resulting TTCP/DCPA/CSH/Li powder was mixed with 0.6 M $(NH_4)_2HPO_4$ setting solution containing 3, 5, or 10 vol % PAA solution with L/P ratio of 0.35 to obtain a TTCP/DCPA/CSH/Li/PAA cement paste. The 3 mm high, 6 mm dia. block samples were prepared from pressure-molding the cement paste under a pressure of 450 kgf.

FIGS. 2 to 5 show the TTCP/DCPA/CSH/Li/PAA blocks prepared above immersed in Hanks' solution for one, two, three and five days, respectively.

TABLE 17

Average diameters (mm) of antibacterial zones of TTCP/DCPA/CSH/Li/PAA blocks immersed in Hanks' solution for different periods of time (days).

|  | 1 d | 2 d | 3 d | 5 d | 7 d |
|---|---|---|---|---|---|
| 3% PAA | 11.0 | 8.0 | 6.3 | 6 | 6 |
| 5% PAA | 10.7 | 10.0 | 6.7 | 6 | 6 |
| 10% PAA | 11.0 | 10.0 | 10.0 | 9.0 | 7.5 |

(Note: The measured antibacterial zones include 6 mm dia. sample)

Results:
(1) The addition of PAA prolongs the antibacterial effect of the TTCP/DCPA/CSH/Li formula.
(2) Sample with setting solution containing 3 vol % PAA shows an antibacterial zone of 11.0 mm after being immersed in Hanks' solution for 1 d; 8.0 mm for 2 d; 6.3 mm for 3 d.
(3) Sample with setting solution containing 5 vol % PAA shows an antibacterial zone 10.7 mm after being immersed in Hanks' solution for 1 d; 10.0 mm for 2 d; 6.7 mm for 3 d.
(4) Sample with setting solution containing 10 vol % PAA shows an anti-bacterial zone 11.0 mm after being immersed in Hanks' solution for 1 d; 10.0 mm for 2 d; 10.0 mm for 3 d; 9.0 mm for 5 d; 7.5 mm for 7 d.

TABLE 18

Average pH values of Hanks' solution wherein TTCP/DCPA/CSH/Li/PAA blocks were immersed for different periods of time (days).

|  | 1 d | 2 d | 3 d | 4 d | 5 d | 6 d | 7 d | 8 d | 9 d | 10 d |
|---|---|---|---|---|---|---|---|---|---|---|
| 3% PAA | 10.1 | 11.1 | 11.0 | 10.8 | 10.6 | 10.5 | 10.4 | 10.3 | 10.2 | 10.1 |
| 5% PAA | 10.1 | 11.1 | 11.2 | 10.8 | 10.7 | 10.5 | 10.5 | 10.3 | 10.2 | 10.1 |
| 10% PAA | 10.2 | 10.7 | 10.6 | 10.7 | 10.9 | 10.7 | 10.7 | 10.6 | 10.3 | 10.2 |

Results:
(1) Average pH values of Hanks' solution are all higher than 10, even higher than 11 in some cases.

TABLE 19

Average weight loss percentages (%) of TTCP/DCPA/CSH/Li/PAA blocks immersed in Hanks' solution for different periods of time (days).

|  | 1 d | 2 d | 3 d | 5 d | 7 d | 10 d |
|---|---|---|---|---|---|---|
| 3% PAA | 19.5 | 25.8 | 29.5 | 35.3 | 41.2 | 43.2 |
| 5% PAA | 17.3 | 22.8 | 28.3 | 31.7 | 42.9 | 45.6 |
| 10% PAA | 15.2 | 23.3 | 28.7 | 40.2 | 48.3 | 49.5 |

Results:
(1) Average weight losses of all samples immersed in Hanks' solution increase with immersion time. After 7 d, more than 40% of the weight is lost.
(2) The weight loss increases with PAA content, especially after 5 d. This result is desirable, since, after the rather quick dissolution of the Li compounds, a highly porous structure is developed in the implant material that can increase the bioresorption rate of the implant.

TABLE 20

Average cell viabilities (sample/DMEM medium ratio = 0.1 g/ml, NIH-3T3) of TTCP/DCPA/CSH/Li/PAA bocks immersed in Hanks' solution for different periods of time (days).

|  | 1 d | 2 d | 3 d | 5 d | 7 d | 10 d |
|---|---|---|---|---|---|---|
| 3% PAA | 49.9 | 50.2 | 50.5 | 51.0 | 54.2 | 54.2 |
| 5% PAA | 55.6 | 55.5 | 55.6 | 58.6 | 59.3 | 60.3 |
| 10% PAA | 64.6 | 65.9 | 64.4 | 65.1 | 68.3 | 86.1 |

Results:
(1) Average cell viability values of all samples immersed in Hanks' solution increase with immersion time, indicating the biocompatibility level continues to increase due to gradual consumption of the Li compound. This result is desirable, since the best result would be that, after the stage of high antibacterial effect, the implant material would gradually recover its biocompatibility level.
(2) The average cell viability values of 10% PAA sample were significantly higher than those of 3% PAA sample and 5% PAA sample. After 10 d, the cell viability values of 10% PAA sample reached 86.1.

Injectability Tests of TTCP/DCPA/CSH/Li Salt/PAA Cement Pastes

Injectability tests were conducted on of TTCP/DCPA/CSH/Li salt/PAA cement pastes. The TTCP/DCPA/CSH/Li salt/PAA cement pastes were prepared by mixing appropriate amounts of "65/35" powder and $Li_2CO_3$ powder ("65/35": $Li_2CO_3$=1:1 by weight) to obtain a TTCP/DCPA/CSH/Li salt mixed powder, wherein TTCP:DCPA=1:1 by mole and TTCP/DCPA:CSH=65:35 by weight. The resulting TTCP/DCPA/CSH/Li salt powder was mixed with 0.6 M, 1 M, 2 M or 3 M $(NH_4)_2HPO_4$ setting solution containing 10 vol % PAA solution with a L/P ratio ranging from 0.35 g/cc to 0.7 g/cc to obtain a TTCP/DCPA/CSH/Li salt/PAA cement paste. The resulting paste was injected into 37° C. water using a 5 cc syringe attaching with or without a surgical needle to test the injectability of the cement pastes. The amount of residual cement (cement remaining in the syringe after normal hand-injection) was measured and considered as an index of injectability of the cement. (The higher amount of residual cement indicates the lower injectability)

TABLE 21

Residual cement (wt %) in syringe after hand-injection of TTCP/DCPA/CSH/Li salt/PAA cement paste through a 5 cc syringe without needle attached.

| $(NH_4)_2HPO_4$ conc. | L/P = 0.35 cc/g | L/P = 0.40 cc/g | L/P = 0.45 cc/g |
|---|---|---|---|
| 0.6M | 78.6 | 10.3 | 0 |
| 1M | 100 | 22.8 | 0 |
| 2M | 100 | 100 | 0 |
| 3M | 100 | 100 | 0 |

TABLE 22

Residual cement (wt %) in syringe after hand-injection of TTCP/DCPA/CSH/Li salt/PAA cement paste through a 5 cc syringe attached with a 11 cm long, 0.6 mm inner dia. "18G" stainless steel needle.

| $(NH_4)_2HPO_4$ conc. | L/P = 0.40 | L/P = 0.45 | L/P = 0.50 | L/P = 0.55 | L/P = 0.60 | L/P = 0.65 | L/P = 0.70 |
|---|---|---|---|---|---|---|---|
| 1M | 100 | 90.1 | 70.8 | 20.2 | 0 | 0 | 0 |
| 2M | 100 | 95.2 | 88.1 | 80.8 | 60.2 | 34.2 | 0 |

Results:
(1) The amount of residual cement in syringe decreases with increasing L/P ratio.
(2) The amount of residual cement in syringe increases with increasing setting solution concentration.

Example 8. Antibacterial Behavior of $CaCO_3$/$Ca_2P_2O_7$/Li Salt Samples

Antibacterial tests were conducted on $CaCO_3$/$Ca_2P_2O_7$/Li salt samples. The $CaCO_3$/$Ca_2P_2O_7$/Li salt samples were prepared by mixing appropriate amounts of $CaCO_3$ and $Ca_2P_2O_7$ powders ($CaCO_3$:$Ca_2P_2O_7$=1:1.27 by weight) with $Li_2CO_3$ powder, wherein $CaCO_3$/$Ca_2P_2O_7$:$Li_2CO_3$=1:1 or 7:3 by weight, to obtain a $CaCO_3$/$Ca_2P_2O_7$/Li salt mixed powder. The $CaCO_3$/$Ca_2P_2O_7$/Li salt mixed powder was mixed with 0.6 M $(NH_4)_2HPO_4$ setting solution with L/P ratio of 0.35 g/cc to obtain a $CaCO_3$/$Ca_2P_2O_7$/Li salt cement paste. The 3 mm high, 6 mm dia. block samples were prepared from pressure-molding the cement paste under a pressure of 450 kgf. The block samples were heated to 600° C. for 1 h or 3 h.

Figure 6:
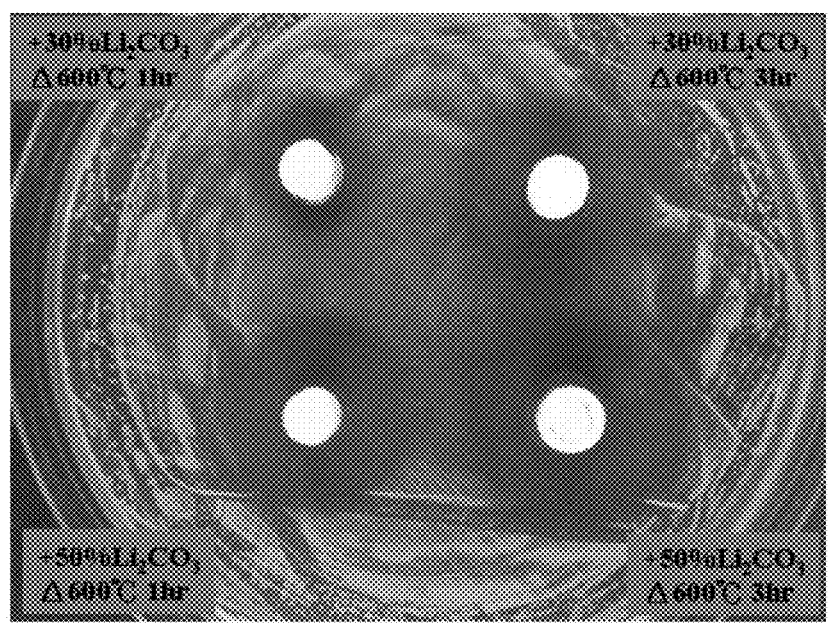
FIG. 6 shows antibacterial zones of CaCO$_3$/Ca$_2$P$_2$O$_7$/Li blocks prepared according to the present invention without immersion.

FIG. 6 shows antibacterial zones of $CaCO_3$/$Ca_2P_2O_7$/Li blocks prepared according to the present invention without immersion.
Results:
(1) Sample containing 70 wt % $CaCO_3$/$Ca_2P_2O_7$ and 30 wt % $Li_2CO_3$ and heated to 600° C. for 1 h shows an antibacterial zone of 12 mm.
(2) Sample containing 70 wt % $CaCO_3$/$Ca_2P_2O_7$ and 30 wt % $Li_2CO_3$ and heated to 600° C. for 3 h shows an antibacterial zone of 18 mm.
(3) Sample containing 50 wt % $CaCO_3$/$Ca_2P_2O_7$ and 50 wt % $Li_2CO_3$ and heated to 600° C. for 1 h shows an antibacterial zone of 19.5 mm.
(4) Sample containing 50 wt % $CaCO_3$/$Ca_2P_2O_7$ and 50 wt % $Li_2CO_3$ and heated to 600° C. for 3 h shows an antibacterial zone of 22.8 mm.

Example 9. Antimicrobial Activity Measurement

Appropriate amount of UV-sterilized sample (either granule or cement) to be tested was put in a 12-well plate, wherein was added 1 ml Tryptone Soya Broth (TSB) with $10^6$ live S. aureusbacteria in each well (concentration: $10^6$ colony-forming units (CFU) per ml). S. aureusbacteria were cultured with the sample anaerobically at 37° C. One cultured without sample was considered as a positive control in each study group. The viability of the bacterial suspensions incubated with different samples was assessed using Tryptone Soya Agar (TSA) solid agar plates. After cultivation for 24 h, broth of each well was sequentially diluted and plated. The growth of bacteria was evaluated after cultivation on agar plates at 37° C. for 24 h. Then colony-forming units (CFU) were counted to calculate concentration using the equation, $$\frac{\text{Colony count on an agar plate (unit} = CFUS)}{\text{Total dilution of tube} * \text{volume plated (unit} = \text{ml)}},$$

and the antimicrobial activity is obtained by the following equation:

Antimicrobial activity={[(Conc. of control group)−(conc. of experiment)]/(Conc. of control group)}×100%

Appropriate amounts of UV-sterilized $Li_3PO_4$ or $Li_2CO_3$ salt were each mixed with 1 ml TSB and tested for their antimicrobial activity values using the aforementioned method. The results are shown in Table 23.

TABLE 23

| Li salt | Li salt amount/TSB (g/ml) | Antimicrobial activity (24 h)(%) |
|---|---|---|
| $Li_3PO_4$ | 0.06 | 98.9 |
| $Li_3PO_4$ | 0.08 | 98.9 |
| $Li_3PO_4$ | 0.10 | 97.4 |
| $Li_3PO_4$ | 0.12 | 98.8 |
| $Li_3PO_4$ | 0.14 | 99.8 |
| $Li_2CO_3$ | 0.06 | 100 |
| $Li_2CO_3$ | 0.08 | 100 |
| $Li_2CO_3$ | 0.10 | 100 |
| $Li_2CO_3$ | 0.12 | 100 |
| $Li_2CO_3$ | 0.14 | 100 |

Results:
(1) The 24 h antimicrobial activity values of $Li_3PO_4$ salt samples with 0.06-0.12 g $Li_3PO_4$ salt in 1 ml TSB are in the range of about 97.4-98.9%. The 24 h antimicrobial activity value of the sample with 0.14 g $Li_3PO_4$ salt in 1 ml TSB reaches 99.8%.
(2) All $Li_2CO_3$ salt samples show a 24 h antimicrobial activity value of 100%.

Appropriate amounts of "65/35" powder were mixed with appropriate amounts of $Li_3PO_4$ or $Li_2CO_3$ salt to form TTCP/DCPA/CSH/Li salt mixed powder with different Li salt ratios. The mixed powder was mixed with 0.6 M $(NH_4)_2HPO_4$ solution to form a cement paste. Prior to being fully hardened, the paste was placed in a stainless steel mold under a pressure of 450 Kgf to squeeze a portion of the liquid out of the paste. After being hardened and removed from the mold, the hardened block was crushed and sieved into granules with a particle size range of about 0.4-1.2 mm. 0.2 g UV-sterilized thus-obtained granular sample was mixed with 1 ml TSB and tested for its antimicrobial activity using the aforementioned method. The results are shown in Table 24.

TABLE 24

| Sample | Antimicrobial activity (24 h) (%) |
|---|---|
| $Li_3PO_4$: 65/35 = 25:75 in weight | 81 |
| $Li_3PO_4$: 65/35 = 50:50 in weight | 100 |
| $Li_2CO_3$: 65/35 = 25:75 in weight | 100 |
| $Li_2CO_3$: 65/35 = 50:50 in weight | 100 |

Results:
(1) For $Li_3PO_4$-containing granular samples, the 24 h antimicrobial activity value increases with increasing $Li_3PO_4$ salt content. The 24 h antimicrobial activity value of the sample containing 50 wt % $Li_3PO_4$ reaches 100%.
(2) The 24 h antimicrobial activity values of both $Li_2CO_3$-containing samples reach 100%.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

The invention claimed is:

1. A bone implant for treating a bony site of a subject, wherein said bone implant is composed of a freestanding block or granules or pieces obtained from said freestanding block; and said bone implant consists of a calcium compound and a lithium compound, and optionally one or more components selected from the group consisting of a growth factor, a bone morphogenetic protein (BMP), living cells, a drug and, a poly(acrylic acid), wherein when the poly (acrylic acid) is present it is present in an amount of 0.01-5% based on the total weight of the bone implant, wherein the lithium compound is configured to dissolve from the bone implant in the bony site after the bone implant is implanted in the bony site of the subject to keep bacteria from approaching the bone implant,
wherein the lithium compound is not lithium halide,
wherein the calcium compound is selected from the group consisting of tetracalcium phosphate, dicalcium phosphate, hydroxyapatite, calcium sulfate dihydrate, calcium sulfate hemihydrate, and a mixture thereof.

2. The bone implant of claim 1, wherein the lithium compound is present in an amount of 5-80% based on the weight of the bone implant.

3. The bone implant of claim 1, wherein the lithium compound is a lithium salt, lithium oxide, lithium amide ($LiNH_2$), or lithium hydroxide.

4. The bone implant of claim 1, wherein the lithium compound is lithium carbonate, lithium sulfate, lithium phosphate, lithium oxide, lithium acetate, lithium hydroxide, lithium nitrate, lithium nitrite, lithium molybdate ($Li_2MoO_4$), lithium tetraborate ($Li_2B_4O_7$), lithium citrate tetrahydrate ($Li_3C_6H_5O_7.4H_2O$), or lithium stearate ($LiC_{18}H_{35}O_2$).

5. The bone implant of claim 1, wherein the lithium compound is lithium carbonate, or lithium phosphate.

6. The bone implant of claim 1, wherein poly(acrylic acid) is present in the bone implant.

7. The bone implant of claim 6, wherein the poly(acrylic acid) has a repeating unit of —$(CH_2$—$C(COOH)H)_n$—, wherein n=50-50000.

8. The bone implant of claim 7, wherein n=1000-5000.

9. The bone implant of claim 1, wherein the bone implant is the freestanding block.

10. The bone implant of claim 9, wherein the freestanding block is a porous block.

11. The bone implant of claim 10, wherein the porous block has a porosity of 50-90 vol %.

12. The bone implant of claim 1, wherein the bone implant is the granules or pieces.

13. The bone implant of claim 12, wherein the calcium compound is selected from the group consisting of tetracalcium phosphate, dicalcium phosphate, calcium sulfate dihydrate, calcium sulfate hemihydrate, or a mixture thereof.

14. The bone implant of claim 12, wherein the granules or pieces have a porosity of 50-90 vol %.

15. A method for treating a subject comprising implanting said granules or said pieces of the free standing block of claim 12 in said subject in need of said treatment.

16. A method of inhibiting bacteria from approaching a bone implant comprising providing a bone implant as set forth in claim 1, and implanting said bone implant in a bony site of a subject, so that the lithium compound dissolves from the bone implant in the bony site to keep bacteria from approaching the bone implant.

* * * * *